(12) United States Patent
Salmisuo et al.

(10) Patent No.: US 10,449,264 B2
(45) Date of Patent: Oct. 22, 2019

(54) DEVICE FOR STERILIZATION OF A FLUID PHASE

(75) Inventors: Mauri Salmisuo, Tuusula (FI); Jani Pettersson, Hyvinkää (FI)

(73) Assignee: STERIS EUROPE, INC. SUOMEN SIVULIIKE

( * ) Notice: Subject to any disclaimer, the term of this patent is extended or adjusted under 35 U.S.C. 154(b) by 751 days.

(21) Appl. No.: 13/468,086

(22) Filed: May 10, 2012

(65) Prior Publication Data

US 2012/0288413 A1 Nov. 15, 2012

(30) Foreign Application Priority Data

May 10, 2011 (EP) ..................................... 11397510

(51) Int. Cl.
*A61L 9/16* (2006.01)
*B01D 46/00* (2006.01)
*B01D 46/42* (2006.01)

(52) U.S. Cl.
CPC ............ *A61L 9/16* (2013.01); *B01D 46/0028* (2013.01); *B01D 46/4263* (2013.01); *A61L 2209/14* (2013.01)

(58) Field of Classification Search
CPC ........................................................ A61L 9/16
USPC ........................................................ 422/120
See application file for complete search history.

(56) References Cited

U.S. PATENT DOCUMENTS

| | | | |
|---|---|---|---|
| 2,825,102 A * | 3/1958 | Hicks et al. ........................ 422/4 |
| 5,251,423 A * | 10/1993 | Turtschan ........................ 53/426 |
| 5,300,098 A * | 4/1994 | Philipot ................. A61F 7/0085 |
| | | | 219/482 |
| 5,441,710 A * | 8/1995 | Marois .......................... 422/307 |
| 2003/0170151 A1* | 9/2003 | Hunter ..................... A61L 2/10 |
| | | | 422/186.3 |
| 2010/0086438 A1* | 4/2010 | Larsson ..................... A61L 2/07 |
| | | | 422/26 |

FOREIGN PATENT DOCUMENTS

| | | | |
|---|---|---|---|
| CN | 2007-32859 | 2/2007 | ................ F24F 6/00 |
| CN | 101829462 | 9/2010 | ............. B01D 46/24 |

(Continued)

OTHER PUBLICATIONS

WO 1995/19216 Obermuller et al. Jul. 1995 english machine translation from WIPO.*

(Continued)

*Primary Examiner* — Donald R Spamer
(74) *Attorney, Agent, or Firm* — Kusner & Jaffe

(57) ABSTRACT

A device in which exhaust fluid from a facility or equipment for treating biologically active material is heated to a temperature of at least 400° C. to kill or denature hazardous agents, and conveyed through a metal filter with no more than 0.1 μm pore size, which is heated, preferably by the fluid, to essentially the same temperature. The relevant temperature is maintained during operation in both the fluid and the filter. Since the filter is dimensioned to trap microbial agents like bacteria and viruses and the temperature of the filter surfaces is sufficient for sterilization, microbial agents are bound to come into contact with said surfaces and a very high degree of sterilization certainty is reached. The filter is welded to the device body to provide a seamless structure. Heating and filtration are both alone sufficient for removing biohazardous agents, so the device provides double security.

15 Claims, 2 Drawing Sheets

(56) References Cited

FOREIGN PATENT DOCUMENTS

| DE | 9400480.3 | 7/1995 | ............. B01D 46/42 |
|---|---|---|---|
| DE | 10217159 | 11/2003 | ............... A61L 9/16 |
| DE | 10348940 | 5/2005 | ............... A61L 9/16 |
| DE | 102004027354 | 2/2006 | ............. B01D 46/16 |
| FR | 2 885 997 A1 | 11/2006 | ............... F23J 15/00 |
| GB | 1 389 369 | 4/1975 | |
| GB | 2 112 298 | 7/1983 | ............. B01D 46/42 |
| WO | WO 95/19216 | 7/1995 | ............. B01D 46/00 |
| WO | WO 96/02281 A1 | 2/1996 | ............... A61L 9/16 |
| WO | WO 98/16263 | 4/1998 | ............... A61L 9/16 |
| WO | WO2008/105696 | 9/2008 | ............. A61L 11/00 |

OTHER PUBLICATIONS

"Sintered Metal Hot Gas Filters" Jha et al. Mott Corporation. Presented at the 4th International Symposium Gas Cleaning at High Temperatures Karlsruhe, Germany Sep. 22-24, 1999.*
Jones. The temperature dependence of the lethal rate in sterilization calculations. J. Fd Technol. (1968) 3, 31-38.*
Sports Whirlpools. Feb. 14, 2008.*
Blain. "Babyproofing my air vents . . . ". Dec. 3, 2008. (Year: 2008).*
Human Translation of Obermuller. WO 95/19216. Jul. 20, 1995. (Year: 1995).*
European Search Report from corresponding European Application No. EP 12 397 514.6; dated Aug. 14, 2012, 4 pages.
European Search Report from corresponding European Application No. 113975106; dated Aug. 10, 2011, 6 pages.
Miller, Duane K., "Pay Attention to Tack and Temporary Welds," Practical Ideas for the Design Professional, Welding Innovation vol. XX, No. 1, 2003.

* cited by examiner

DEVICE FOR STERILIZATION OF A FLUID PHASE

FIELD OF THE INVENTION

The present invention relates to the sterilization of phases comprising gases and/or vapors and suspended particles. The invention is directed to a device for sterilization of streams of the mentioned matter.

BACKGROUND OF THE INVENTION

As various pathogenic microbes and substances are being treated in dedicated facilities, such as laboratories, research facilities, hospitals, glove boxes and other special containment areas, and also in equipment for biowaste destruction, it is of increasing importance to ensure that none of these agents escapes outside such facilities or equipment at any time during the various processing stages. Autoclaves are typically used for sterilization of various media, equipment, tools and waste materials.

During use of such equipment or facilities, gases and vapors, typically air and steam, are led both into the facility and out of it. A particular case is the exhaust from an autoclave used for sterilization. During an operational process, the autoclave goes through various cycles of evacuation and repressurization, whereby the risk of still viable hazardous agents escaping through an exhaust channel is obvious, in particular during the early stages of the process when the specified sterilization temperature has not yet been reached. To decrease this risk, filters are often arranged in the exhaust line. An effective way of ensuring that the exhaust stream is sterile is to provide an incinerator in the exhaust line, but open flame incinerators are not easy to operate and not cost-effective, and they pose other risks.

Sterilization in the context of the present discussion includes the killing of microbes including bacteria and viruses so as to render them non-pathogenic, as well as the destruction of other biological agents that may cause harmful effects. Exhaust fluids in this context mean gases which are non-condensable under the normal operational conditions of the device to which the exhaust line is connected, such as atmospheric gases, as well as condensable vapors, and also any particles suspended in these, and which exit a facility or equipment in order to be sterilized in accordance with the invention.

In International patent application WO2008/105696, a device and process for treating an autoclave exhaust stream are disclosed. The invention disclosed in WO2008/105696 is based on the arrangement of two filters in series in the exhaust line, and a heater between the filters for evaporating condensate that tends to form in the line. With the use of the heater, the condensate can be driven through a hydrophobic filter which will not allow liquid water through, and the condensate can also be heated to sterilization temperature.

In international patent application WO 98/16263 are disclosed a method and apparatus for sterilizing air to be used for e.g. pneumatic medical instruments, cleanrooms and aircraft cabins. The device comprises a replaceable filter.

SUMMARY OF THE INVENTION

In order to ensure maximum sterility, according to the present invention a device has been developed in which exhaust fluid from equipment or a facility for treating biologically active material is heated to a temperature at least sufficient to kill or denature hazardous agents, and conveyed through a filter which is heated, preferably by the fluid, to essentially the same temperature. The relevant temperature is maintained during operation in both the fluid and the filter. Since the filter is dimensioned to trap microbial agents like bacteria and viruses and the temperature of the filter surfaces is sufficient for sterilization, microbial agents are bound to come into contact with said surfaces and a very high degree of sterilization certainty is reached.

According to the invention, a device is provided which has a body, an inlet port, a space provided with a heat source for heating a fluid flowing through the space which comprises a meandering channel for ensuring effective heat transfer, at least one metal filter unit which can be heated to the desired fluid temperature which is at least 400° C., and an exit port for fluid which has passed through the filter unit(s).

The filter unit or units are seamlessly joined to the body of the device by welding without the use of gaskets. Eliminating the gaskets makes possible the utilization of temperatures in excess of 600° C.

DETAILED DESCRIPTION OF A PREFERRED EMBODIMENT

Figure 1:
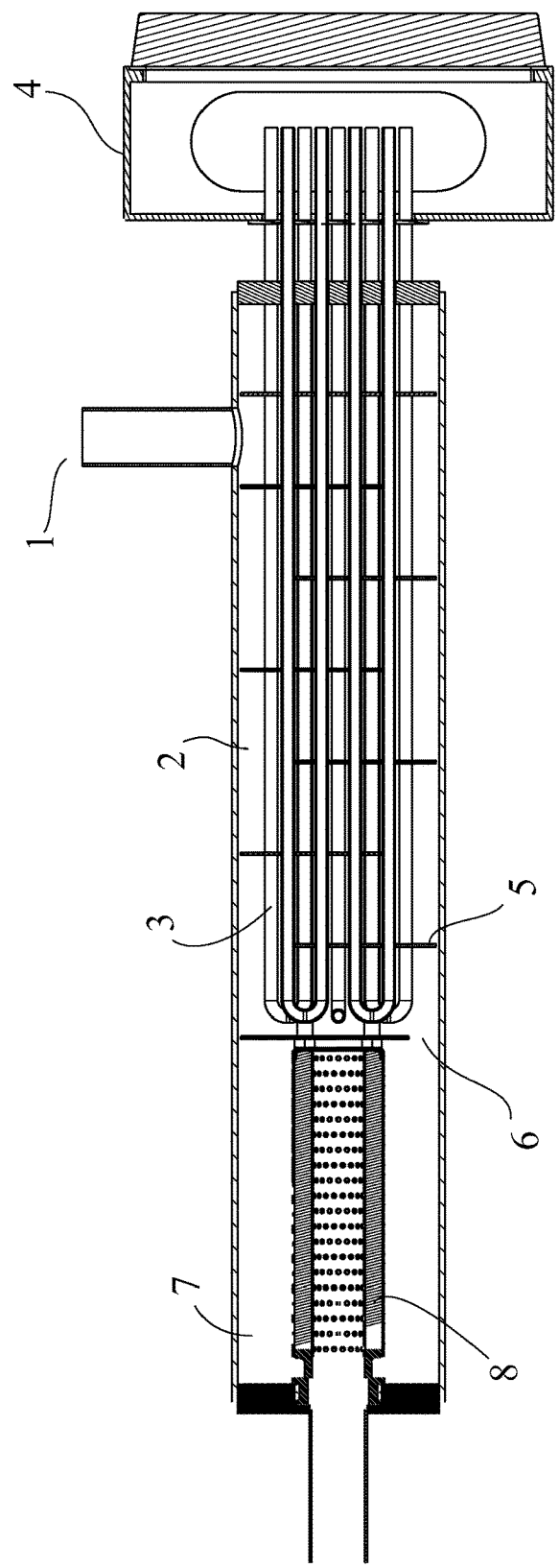
FIG. 1 is a longitudinal section of a device according to the invention.

In the following, the invention is described in detail with reference to the attached drawings. FIG. 1 shows a longitudinal section of a device according to the invention. Fluid enters through inlet port 1, which is connected via suitable tubing to an exhaust port of e.g. an autoclave or a device for the destruction of biological waste. The inlet port leads to the inside of a heating section 2, which comprises heating rods 3. These are preferably resistive metal heating elements connected to an electrical supply unit 4, the details of which are not shown but well known to the skilled person. As is understood by the person skilled in the art, the device for heating the fluid may be in any form which ensures adequate heating of the fluid and is compatible with the process according to the invention. The heating section 2 is provided with baffles 5 in order to form a meandering channel ensuring advantageous conditions for heat transfer. The distance between the heating elements is based on the maximum flow of the fluid.

The outlet 6 of the heating section leads to a filtering section 7, in which is provided a filter unit 8. A single filter unit is shown in FIG. 1, but arrangements involving several parallel units are also possible. The pore size is 0.1 μm or less.

Preferably, the material of the filter unit is stainless steel. Other metal alloys may be used as required, taking into account the desirability to obtain a seamless, welded structure.

Suitable metal filter units are available from e.g. the Pall Corporation, New York.

During operation, the filter unit is essentially in thermal equilibrium with the heated fluid flowing through it. According to a preferred embodiment of the invention, the thermal equilibrium is achieved by including in the process a preconditioning stage, during which a vacuum pump pulls sterile, filtered atmospheric air through the heating and filter section.

Figure 2:
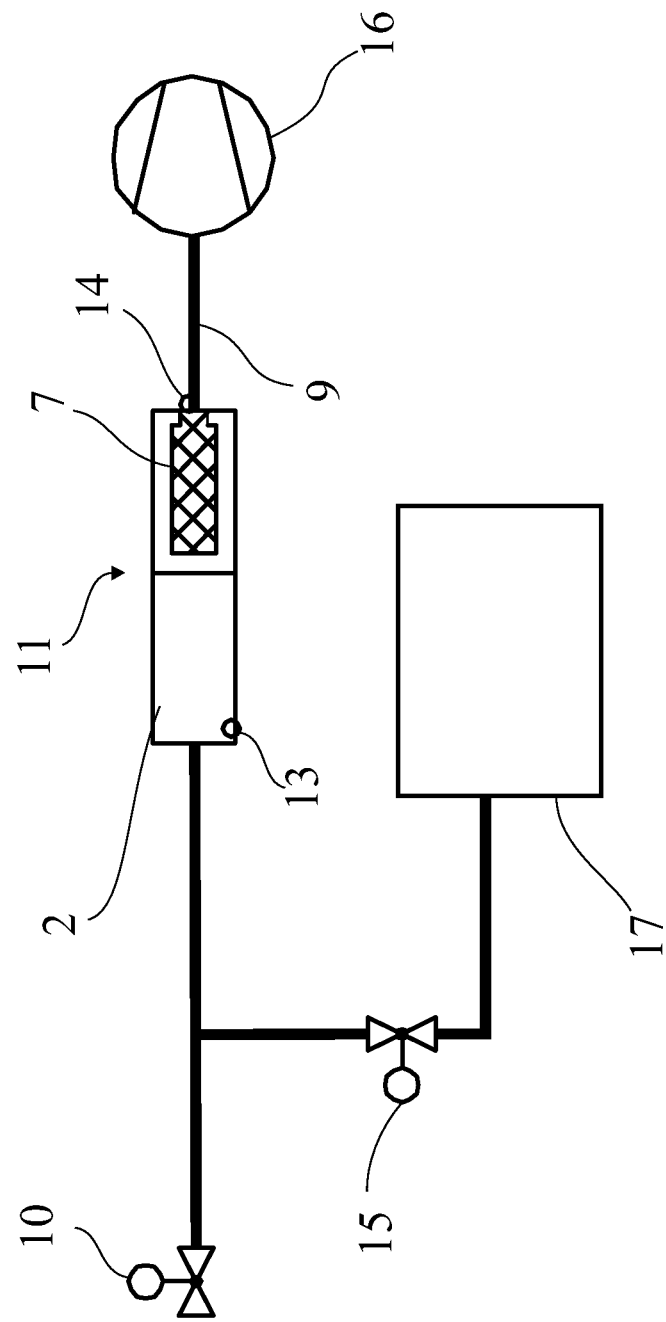
FIG. 2 is a schematic view of a tubing arrangement associated with the device according to the invention.

In FIG. 2, a setup involving a device according to the invention is shown. Vacuum pump 16 is connected to line 9. During the preconditioning stage, valve 10 is open, allowing filtered ambient air to flow through the device 11, while valve 15 is closed, preventing fluid from entering the heating and filtering section from source 17, which may be e.g. an autoclave chamber. Heating section 2 is operable and the temperature of the flow is monitored at a measuring point 13 in the heater but upstream of the filter and at a measuring point 14 downstream from the filter. From the temperature difference between these measurements, the filter temperature can be deduced as the filter unit is heated by the air flow flowing through it. Only when the filter unit has reached its operating temperature, i.e. when the temperature values at measuring points 13 and 14 are acceptable, valve 10 may be closed and valve 15 opened, allowing the flow to be sterilized to enter the device.

With the filter unit at operating temperature, agents entering the device encounter already in the heating section a temperature which is normally sufficiently high to eliminate the viability of bacteria and viruses, and to effect degeneration of biologically active structures like pyrogens and prions where applicable. The relevant temperature is determined by the skilled person according to the conditions and biological agents involved in each case. The fluid temperature at the downstream end of the heating section is above 400° C.; preferably above 600° C.

Finally, surface contact with the filter unit or units at essentially the same temperature ensures that no viable harmful agents are released to the atmosphere.

After the fluid stream has passed through the unit, it may be cooled by spraying water into the stream through a nozzle, or in any other suitable way, as is known to the skilled person.

The device according to the invention may be used for sterilizing a fluid leaving a processing device or facility, but it may also be used for decontamination of inflowing fluid to a facility or apparatus if necessary.

Example

The efficiency of the device for sterilization according to the present invention was tested. The device used in the tests corresponds to that shown in FIG. 1. Biologically active endotoxin (*E. coli* O55:B5 Endotoxin) was fed into the device and the endotoxin concentration was measured from the outcoming fluid. Biologically active endotoxin was measured using a validated kinetic chromogenic Limulus Amebosyte Lysate assay (Kinetic-QCL; Lonza, Walkerswille, Md., USA). The pore size of the filter unit was 0.1 μm. Five different tests with different test arrangements were performed as follows;

I. The endotoxin was fed through the heating unit, the filter unit was taken off—with heating (420° C.);
II. The endotoxin was fed through the heating unit—no heating;
III. The endotoxin was fed through the heating unit and the filter unit—no heating;
IV. The endotoxin was fed through the heating unit and the filter unit—with heating (420° C.);
V. The endotoxin was fed through the filter unit—no heating The test results are shown in Table 1 below.

TABLE 1

| Test results | | | | | |
|---|---|---|---|---|---|
| Test # | I | II | III | IV | V |
| Heating section(* | + | + | + | + | − |
| Filter unit(* | − | − | + | + | + |
| Heating (420° C.) | yes | no | no | yes | no |
| Endotoxin concentration of the outcoming fluid(** | 0 | 360 EU/ml | 0 | 0 | 0 |

(*The presence of the heating section and/or filter unit in the device: yes (+), no (−)
(**Zero (0) means that no endotoxin was present in the outcoming fluid As can be seen from Table 1, the device for sterilization of a fluid phase according to the present invention combines two effective sterilization operations (heating and filtration). The arrangement provides redundancy, since effective sterilization occurs even if one component, heating or filtration, would fail.

Having described the invention, the following is claimed:

1. A device for the sterilization of a fluid comprising one or more of the following: gas, suspended particles and vapors, said device comprising:

a longitudinal tubular body having an inlet port at a first end of a heating section of said body and an exit port at a second end of a filtration section of said body, a flow path extending through said body being defined between said inlet port and said exit port, said heating section of said body sharing a central axis with said filtration section of said body;

a heating element extending from said first end of said heating section into said heating section of said body, said heating element extending along a major length of said body;

a plurality of spaced-apart baffles disposed in said heating section of said body, each of said plurality of baffles traversing said heating element in a direction generally perpendicular to a longitudinal axis of said heating element, each of said plurality of baffles having a free end spaced from an inner surface of said body, adjacent baffles extending in opposite directions such that free ends thereof are disposed on generally opposite sides of said body to define a meandering channel through said body from the first end of said heating section to a second end of said heating section wherein fluid flowing through said meandering channel repeatedly traverses said heating element as said fluid flows from said first end of said heating section to said second end of said heating section;

at least one metal filter unit disposed in said filtration section of said body, said at least one metal filter unit being seamlessly welded to said body and said at least one metal filter unit having a pore size of 0.1 μm or less; and a first temperature sensor disposed at said inlet port of said body and a second temperature sensor disposed at said exit port of said body, wherein said device is designed to heat said fluid to a temperature of at least 600° C.

2. The device defined in claim 1, wherein said at least one metal filter unit is disposed between said second end of said heating section and said exit port of said body.

3. The device defined in claim 2, wherein said at least one metal filter unit is axially aligned with said heating element.

4. The device defined in claim 1, wherein a length of said tubular body is greater than a width of said tubular body.

5. A system for sterilizing a fluid comprising one or more of the following: gas, suspended particles and vapors, said system including:
 a longitudinal tubular body having an inlet port at a first end of a heating section of said body, an exit port at a second end of a filtration section of said body, and a flow path extending through said body through which a first stream of filtered ambient air and a second stream of said fluid respectively flow, the flow path being defined between said inlet port and said exit port, said heating section of said body sharing a central axis with said filtration section of said body;
 a heating element extending from said first end of said heating section into said heating section of said body, said heating element extending along a major length of said body;
 a plurality of spaced-apart baffles disposed in said heating section of said body, each of said plurality of baffles traversing said heating element in a direction generally perpendicular to a longitudinal axis of said heating element, each of said plurality of baffles extending partially across said opening of said body to define a gap between an end of said baffle and an inner surface of said body, adjacent baffles extending in opposite directions such that gaps defined by adjacent baffles are disposed on generally opposite sides of said body to define a meandering channel through said body from the first end of said heating section to a second end of said heating section, wherein said first and second streams respectively flow through said meandering channel from said first end of said heating section to said second end of said heating section, said first and second streams repeatedly traversing said heating element in said meandering channel until exiting said meandering channel at said second end of said heating element;
 at least one metal filter unit disposed in said filtration section of said body, said at least one metal filter unit being configured to receive said first and second flows respectively from said heating element, said at least one metal filter unit being seamlessly welded to said body and said at least one metal filter unit having a pore size of 0.1 µm or less;
 an inlet conduit having a first end and a second end, said first inlet conduit end being connected to said inlet port of said body to respectively supply said first and second streams to said inlet port, said second inlet conduit end being directly connected to a supply of said first stream, the inlet conduit comprising a first valve at said second inlet conduit end, said first valve being configured to control said supply of said first stream to said inlet conduit and close when said at least one metal filter unit reaches a temperature greater than or equal to a predetermined operating temperature to inhibit said first stream from passing through said inlet conduit to said body; and
 a source conduit having a first end and a second end, the second source conduit end being connected to a source chamber that is configured to supply said second stream to said source conduit, the first source conduit end being connected to a portion of said inlet conduit located between the first inlet conduit end and the second inlet conduit end, the source conduit having a second valve between the first and second source conduit ends, the second valve being configured to control a supply of said second stream to said inlet conduit and open when said at least one metal filter unit reaches said temperature greater than or equal to said predetermined operating temperature to allow said second stream to pass through said inlet conduit and be supplied to said body.

6. The system defined in claim 5, wherein said source chamber is in an autoclave.

7. The system defined in claim 5, wherein the inlet conduit is directly connected to the first stream through said first valve.

8. The system defined in claim 5, wherein said source chamber is positioned upstream of said filtration section.

9. The system defined in claim 5, wherein said source chamber is positioned upstream of said tubular body.

10. A device for the sterilization of a fluid comprising gas, suspended particles and possibly vapors, said device comprising:
 a longitudinal tubular body having an inlet port at a first end of a heating section of said body, an exit port at a second end of a filtration section of said body, and a flow path extending through said body that is defined between said inlet port and said exit port, said heating section of said body sharing a central axis with said filtration section of said body, said heating section having a space for conveying the fluid in intimate contact with heated surfaces, said space provided with baffles forming a meandering channel;
 a heating element extending from said first end of said heating section into said heating section of said body, said heating section extending along a major length of said body; and
 a metal filter unit disposed in said filtration section of said body, the filter unit being seamlessly welded to the body downstream from said heating section, said filter unit having a pore size of 0.1 µm or less,
 wherein said heating section is configured to heat the filter unit to at least 400° C.

11. The device defined in claim 10, further comprising:
 temperature sensors positioned upstream and downstream relative to the filter unit.

12. The device defined in claim 10, further comprising:
 a first temperature sensor disposed at said inlet port of said body; and
 a second temperature sensor disposed at said exit port of said body.

13. The device defined in claim 12, wherein the heating section is disposed in the flow path, and
 wherein the filter unit is disposed in the flow path at a location downstream from said heating section.

14. The device defined in claim 13, wherein said heating element is further configured to heat said fluid to a temperature of at least 600° C.

15. The device defined in claim 14, wherein the baffles are spaced-apart,
 wherein each of said baffles traverses the heating element in a direction generally perpendicular to a longitudinal axis of the heating element,
 wherein each of the baffles has a free end spaced from an inner surface of the body,
 wherein adjacent ones of the baffles extend in opposite directions such that the free ends thereof are disposed on generally opposite sides of the body to define a meandering channel through the body from the first end of the heating section to a second end of the heating section, and
 wherein the fluid flowing through the meandering channel repeatedly traverses the heating element as the fluid flows from the first end of the heating section to the second end of the heating section.

* * * * *